(12) United States Patent
Tumey (10) Patent No.: US 6,678,557 B1
(45) Date of Patent: Jan. 13, 2004

(54) SYSTEM AND METHOD FOR BODY FAT MANAGEMENT

(75) Inventor: David M. Tumey, San Antonio, TX (US)

(73) Assignee: TVX Internet Services, Inc., San Antonio, TX (US)

(*) Notice: Subject to any disclaimer, the term of this patent is extended or adjusted under 35 U.S.C. 154(b) by 0 days.

(21) Appl. No.: 09/933,030

(22) Filed: Aug. 20, 2001

(51) Int. Cl.[7] .................................................. A61N 1/00
(52) U.S. Cl. ............................................................. 607/2
(58) Field of Search .................................... 607/1–156

(56) References Cited

U.S. PATENT DOCUMENTS 5,913,836 A * 6/1999 Groux

2002/0055762 A1 * 5/2002 Gliner
2002/0058906 A1 * 5/2002 Lebel et al.

* cited by examiner

Primary Examiner—Scott M. Getzow
(74) Attorney, Agent, or Firm—Wayne J. Colton, Inc.

(57) ABSTRACT

An integrated weight loss system generally comprises an electronic stimulation device in communication through the Internet with a host server. The electronic stimulation device serves to stimulate reduction of fat cells as a key part of a weight loss protocol. The protocol takes advantage of the Internet to combine new and previously available weight loss modalities in a manner designed to obtain greater weight loss success than likely through individual usage of the component modalities. Additionally, the integrated weight loss system and the protocol take advantage of the Internet to provide the user with a unique compliance monitoring scheme designed to promote as high as possible weight loss success.

11 Claims, 6 Drawing Sheets

# SYSTEM AND METHOD FOR BODY FAT MANAGEMENT

FIELD OF THE INVENTION

The present invention relates to systems and methods for weight loss and body fat management. More particularly, the invention relates to methods and apparatus wherein the Internet is utilized as delivery channel for protocol instructions, device control signals and compliance information for a weight loss therapy as well as a mechanism for interconnection of the therapy's constituent components—all in a manner designed to produce weight loss results not available through individualized or uncoordinated usage of the various components.

BACKGROUND OF THE INVENTION

Collagen-based formulas have been reported to increase lean body muscular mass and promote fat loss when taken as a dietary supplement. Although the exact physiology is not known, it is believed that the collagen-based formula enhances the known physiological processes for the metabolism of fat and muscle as influenced by the complex interplay between insulin, exercise and stress and other hormones. Regardless of the physiological basis, however, the reported weight loss results speak for themselves.

Other unrelated studies have reported that persons receiving mild electrical currents into their bodies have experienced weight loss. While the underlying causes for the weight loss are not completely understood, it is believed that the electrical currents cause the sympathetic nervous system to produce catecholemines, which in turn attach to receptor sites on fat cells. As a result, it is believed that free fatty acids are released into the blood stream. Depending on the user's exercise regime and dietary habits, the released free fatty acids may be converted to more useful products.

While each of the foregoing modalities are simple and require little time to practice, many people still fail in their diets for lack of consistent compliance. It is therefore an overriding object of the present invention to combine these and other routines in a manner uniquely designed to promote maximum compliance with a weight loss protocol. It is a further object of the present invention to utilize the Internet as the mechanism for delivery to user's of a such a weight loss protocol.

SUMMARY OF THE INVENTION

In accordance with the foregoing objects, the present invention—a system for body fat management—generally comprises a source of electrical current and a controller in communication with the source through a global communication network. The source comprises a plurality of electrical conductors for imparting the electrical current into a user's body, thereby stimulating the reduction of fat cells. The controller may be adapted to effect control over both the amplitude and the frequency of the current signal and is adapted to monitor a user's progress according to a related protocol and weight loss goals and, in response to such monitoring, generate and transmit appropriate electronic messages.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 1:
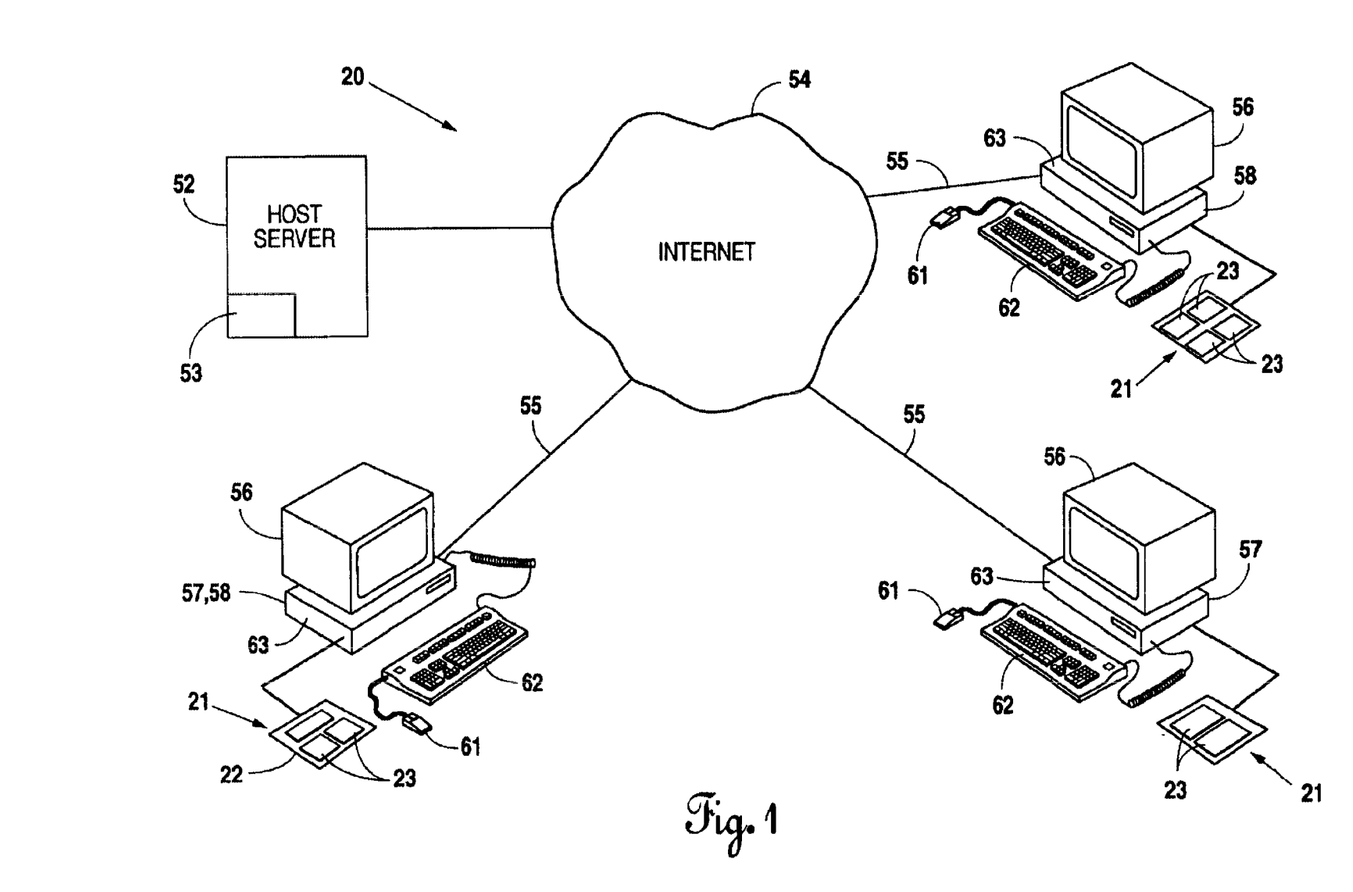
FIG. 1 shows, in a functional block diagram, an overview of the system of the present invention.

Referring now to the figures, and to FIG. 1 in particular, the integrated weight loss system 20 of the present invention is shown to generally comprise an electronic stimulation device 21 in communication through the Internet 54 with a host server 52. As will be better understood further herein, the electronic stimulation device 21 serves to stimulate reduction of fat cells as a key part of a novel weight loss protocol 64. As also will be better understood further herein, this protocol 64 takes advantage of the Internet 54 to combine new and previously available weight loss modalities in a manner designed to obtain greater weight loss success than is likely through individual usage of the component modalities. Additionally, the integrated weight loss system 20 and the protocol 64 of the present invention take advantage of the Internet 54 to provide the user with a unique compliance monitoring scheme 87 designed to promote as high as possible weight loss success.

Figure 2:
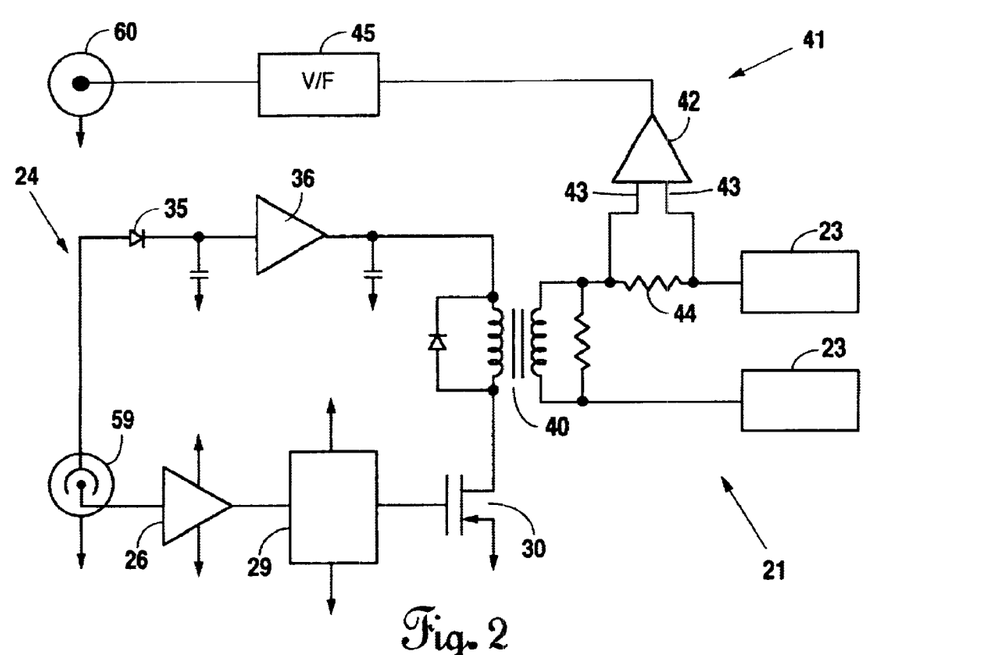
FIG. 2 shows, in a schematic block diagram, an electronic stimulation device utilized in the system of FIG. 1.

As shown in FIG. 2, the preferred embodiment of the electronic stimulation device 21 generally comprises a stimulation control module 24, adapted to deliver a low current voltage to the user's body, and a spectral analysis circuit 41, adapted to determine the optimum frequency for conduction into the user's body of the low current voltage Although those of ordinary skill in the art will recognize many substantially equivalent alternatives, the preferred embodiment of the invention utilizes a plurality of stainless steel foot plates 23 embedded in the top of a digital scale 22 to provide electrical contact between the stimulation control module 24 and the user's feet. In this manner, weight readings utilized according to the protocol 64 of the present invention are guaranteed to be available at the time of therapy.

Figure 3:
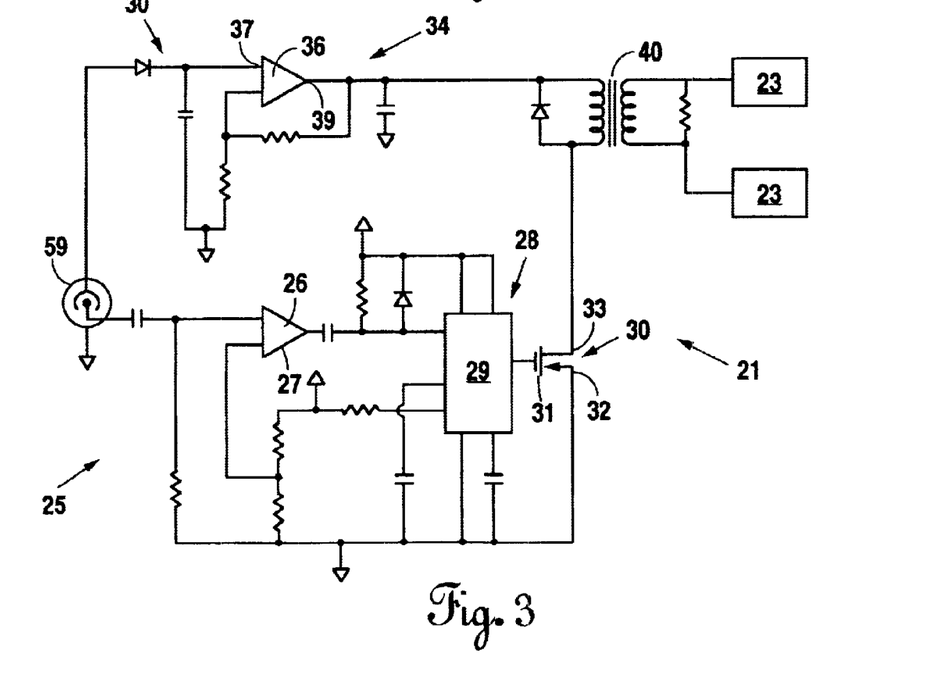
FIG. 3 shows, in an electrical schematic, details of the electronic stimulation device of FIG. 2.

As shown in FIG. 3, the preferred embodiment of the stimulation control module 24 comprises a frequency control circuit 25, for controlling the frequency of the delivered current signal, and a voltage control circuit 34, for controlling the amplitude of the delivered current signal. In particular, the frequency control circuit 25 comprises an operational amplifier 27, configured as a comparator 26, which in turn drives a 555 integrated circuit timer 29, configured as a monostable oscillator 28, according to the level of an input signal. Although those ordinary skill in the art will recognize other alternative embodiments, Applicant has found it convenient to interface the input to the comparator 26 to one side of a stereo audio output port 59 from a sound card 58 of the user's personal computer 56. In any case, the output from the monostable oscillator 28 is utilized to drive the gate 31 of a medium power MOSFET 30. The transistor's source 32 and drain 33 circuits are in series with a 10 to 1 step-up transformer 40, which interfaces the stimulation control module 24, to the foot plates 23.

The other side of the stereo audio output port 59 is connected an envelope detector 35 configured to drive the positive input 37 of an operational amplifier 36, the output 39 of which is also connected to the step-up transformer 40. In this manner, both the amplitude and the frequency of the signal generated through the step-up transformer 40 may be controlled by software resident the user's personal computer 56 or through web content 53 at a central host server 52. While it is noted that the actual control of the stimulation control module 24 may be handled in the local environment of the user's personal computer 56, it is nonetheless desirable for reasons that will be more apparent further herein that the user's personal computer 56 be provided with Internet connectivity 55 in order to take maximum advantage of the features available through the full protocol 64 of the present invention.

Finally, as shown in FIG. 2, the spectral analysis circuit 41 generally comprises a current amplifier 42 having inputs 43 connected across a shunt resistor 44 in the output of the step-up transformer 40. In this manner, current flow through the foot plates 23 into the user's feet may be monitored by the current amplifier 42. The output from the current amplifier 42 is then communicated through a voltage to frequency converter 45 to the audio input port 60 of the sound card 58 in the user's personal computer 56. In operation, software resident the personal computer 56 or, in the alternative, resident the host server 52 may be utilized to generate a sweep of frequencies (through the frequency control circuit 25) while the spectral analysis circuit 41 is utilized to determine which frequency or frequencies are best conducted into the feet of the user.

Figure 4:
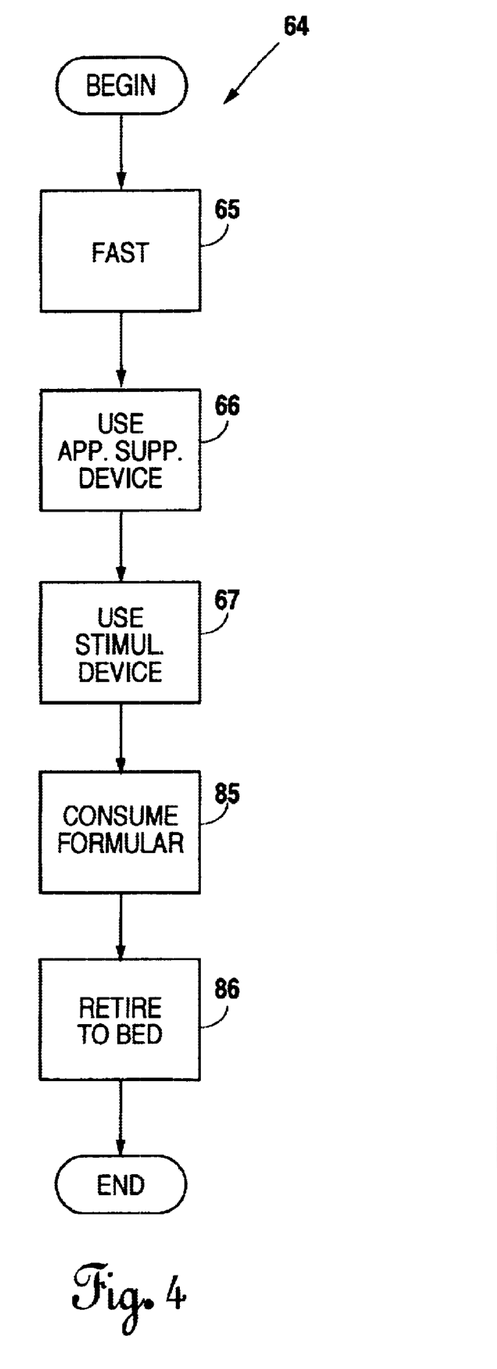
FIG. 4 shows, in a flowchart, on overview of the preferred protocol for utilization of the system of FIG. 1.
Figure 5:
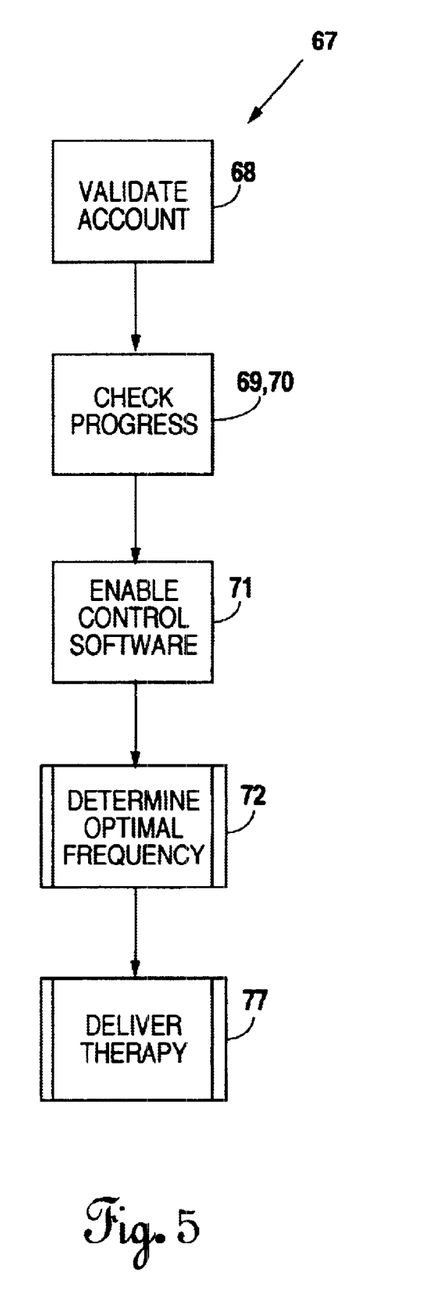
FIG. 5 shows, in a flowchart, an overview of the preferred method for utilization within the protocol of FIG. 4 of the stimulation device of FIG. 2.

Referring now to FIG. 4, the preferred protocol 64 of the present invention is detailed. According to the preferred protocol 64, a user wishing to lose weight with the assistance of the present invention is directed to fast for at least a three hours prior to bedtime (step 65). If, however, the user should have difficulty abstaining from food or carbonated or sugary beverages for the full three hour period, the present invention also comprises the utilization of an electronic appetite suppressor (step 66). Such an electronic appetite suppressor generally comprises a headphone type device adapted to produce a mild electrical current, at known acupuncture points near the ears which is thought to induce in the user a sense of well being similar to that obtained through acupuncture techniques. In any case, the user then makes use of the electronic stimulation device 21 during the final 15 minutes prior to bedtime (step 67). Use of the electronic stimulation device 21 (as described in greater detail further herein) is thought to activate the sympathetic nervous system in the production of catecholemines. The produced catecholamines then attach to receptor sites on the user's fat cells, thereby releasing free fatty acids into the blood stream. Upon completion of the electronic stimulation therapy, the user may consume a collagen-based formula (step 85) and retire to bed (step 86). As the user sleeps, the collagen-based formula utilizes the released free fatty acids for tissue, muscle and bone repair. In this manner, body fat is effectively is redistributed and converted into more healthy tissues As shown in FIG. 5, the use of the electronic stimulation device 21 preferably begins with the validation of the user's account information as maintained on the host server 52 (step 68). In particular, the user may enter a secure wet site through standard user name and password protocols whereafter the software at the host server may confirm that the user is paid in full, has available credit with the service provider or is otherwise entitled to make use of the integrated weight loss system 20. At this point, it is desirable that provision be made to check the user's progress as a member of the service. To this end, a weight measurement may be uploaded to the host server 52 (step 69) and/or a body fat analysis may be performed (step 70). In the case of weight measurement, the user may use his or her keyboard to manually enter weight data into the system or, in the case of a more fully integrated stimulation device 46 as described in greater detail further herein, weight data may be automatically transmitted to the host server 52. In the case of body fat analysis, standard electrical impedance measurement tests may be performed through the foot plates 23, whereafter uploaded electrical impedance measurements may be utilized at the host server 52 to estimate the user's body fat. In any case, the user's connectivity 55 through the Internet 54 to the host server 52 presents the opportunity for the service provider to make comparisons between the user's current weight and body condition and the user's targeted condition. Importantly, this feature allows for "good advice" and "words of encouragement" to be generated at the host server 52 and delivered through the Internet 54 to the user.

Regardless of whether the user's progress is checked, a system control screen is presented on the user's personal computer 56 through which step-by-step user instructions for the conduct of the stimulation therapy may be provided (step 71). As will be appreciated by those of ordinary skill on the art, the system control screen may be entirely generated as web content 53 resident the host server 52. In the alternative, however, the host server 52 may transmit a preferably encrypted one time access code to the user's personal computer 56, thereby enabling the launch of locally maintained application software 63. In this alternative, Internet latency is less at the time of therapy to disrupt the therapy at a critical stage. Most preferably, however, the host server 52 may generate an application program for download to the user's personal computer 56, where the program may run locally. As known to these of ordinary skill in the art, such applications may be generated utilizing the Macromedia trademark "FLASH" standard or the substantial equivalent thereof.

Figures 6, 7:
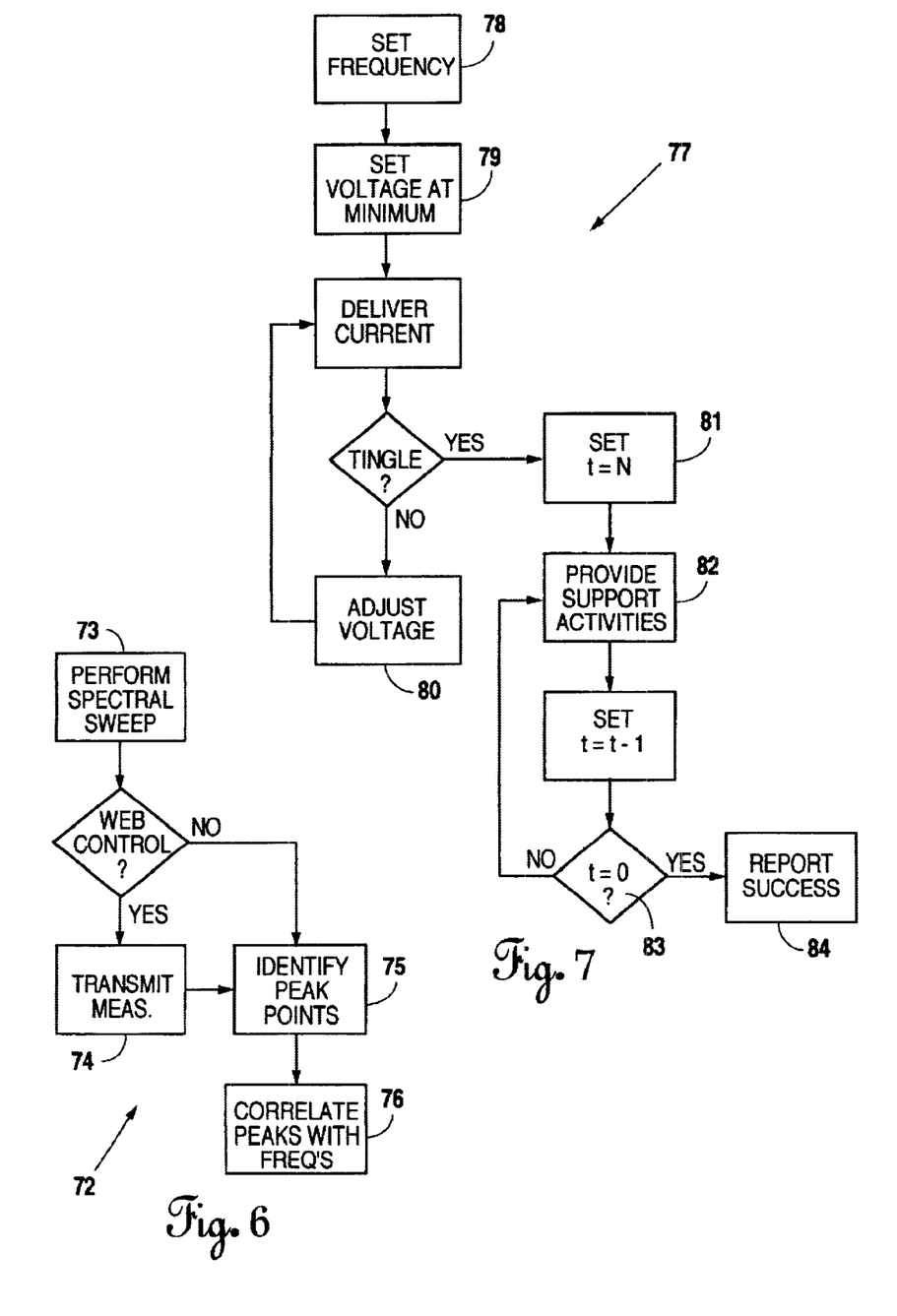
FIG. 6 shows, in a flowchart, certain details of the method of FIG. 5.
FIG. 7 shows, in a flowchart, certain other details of the method of FIG. 5.

Once the system control screen has been presented to the user, the user is instructed to place one foot only on each of the two plates 23 and to sit comfortably in a chair. The appropriate treatment frequency is then determined (step 72)

and the therapy delivered (step 77), each as described in greater detail further herein. Although those of ordinary skill in the art will recognize that the treatment frequency may be manually selected or may be determined a priori based upon empirical data, it is preferred that an analysis be performed each time the electronic stimulation device 21 is utilized in order to determine which frequency or frequencies are best conducted into the user's feet at that time. In this manner, factors such as hydration and the like may be accounted for, thereby ensuring that user will receive the maximum benefit of the described protocol 64. To this end, a low voltage and low current a spectral sweep preferably encompassing frequencies from about 100 Hz to about 10 kHz is first performed (step 73). During the spectral sweep, the spectral analysis circuit 41 is utilized to measure the current conducted into the user's feet. The measurements are then transmitted to the host server 52 (step 74) unless the embodiment relies upon local application software 63. In any case, the peak energy point or points are identified (step 75) and correlated with the frequency or frequencies responsible for their generation (step 76).

Once the treatment frequency has been determined, the therapy is delivered by first setting the therapy frequency according to the previous determination (step 78). Under the control of the voltage control circuit 34, the lowest level current is then delivered at the set treatment frequency (step 79) through the foot plates 23 to the user. The system control screen then interrogates the user to determine whether the user can feel a slight "tingling" sensation in his or her feet. At this time, the user is directed to use his or her computer's pointing device 61 or keyboard 62 to adjust a graphically presented slider button until the desired sensation is felt (step 80). Upon generation of sufficient current to produce a tingling sensation indicative of current flow through the user's feet, a treatment timer is started in order to deliver 8 to 20 minutes of therapy to the user (step 81).

At this point the Internet 54 may be utilized in a unique opportunity to provide motivational activities for the user (step 82). For example, the host server 52 may generate and deliver "good advice" and "words of encouragement," thereby facilitating the passage of the necessary treatment time. Likewise, the host server 52 may be utilized to connect the user with other users in a brief Internet chat session, thereby allowing the user to engage in discussions with others facing similar weight control issues. While those with ordinary skill in the art will recognize that such Internet chat sessions may be offered on an unrestricted basis to members of the service, it may desirable to limit access to only that time during which the electronic stimulation therapy is being delivered. In this manner, the sense of community to be obtained through the Internet chat session may be utilized as a motivating factor for the user's consistent compliance. In any case, once the treatment timer has expired (step 83) the host server 52 preferably generates and delivers final encouragement for the user (step 83) and the user's successful completion is reported to the host server 52 (step 84) for compliance monitoring, as detailed further herein.

Figure 8:
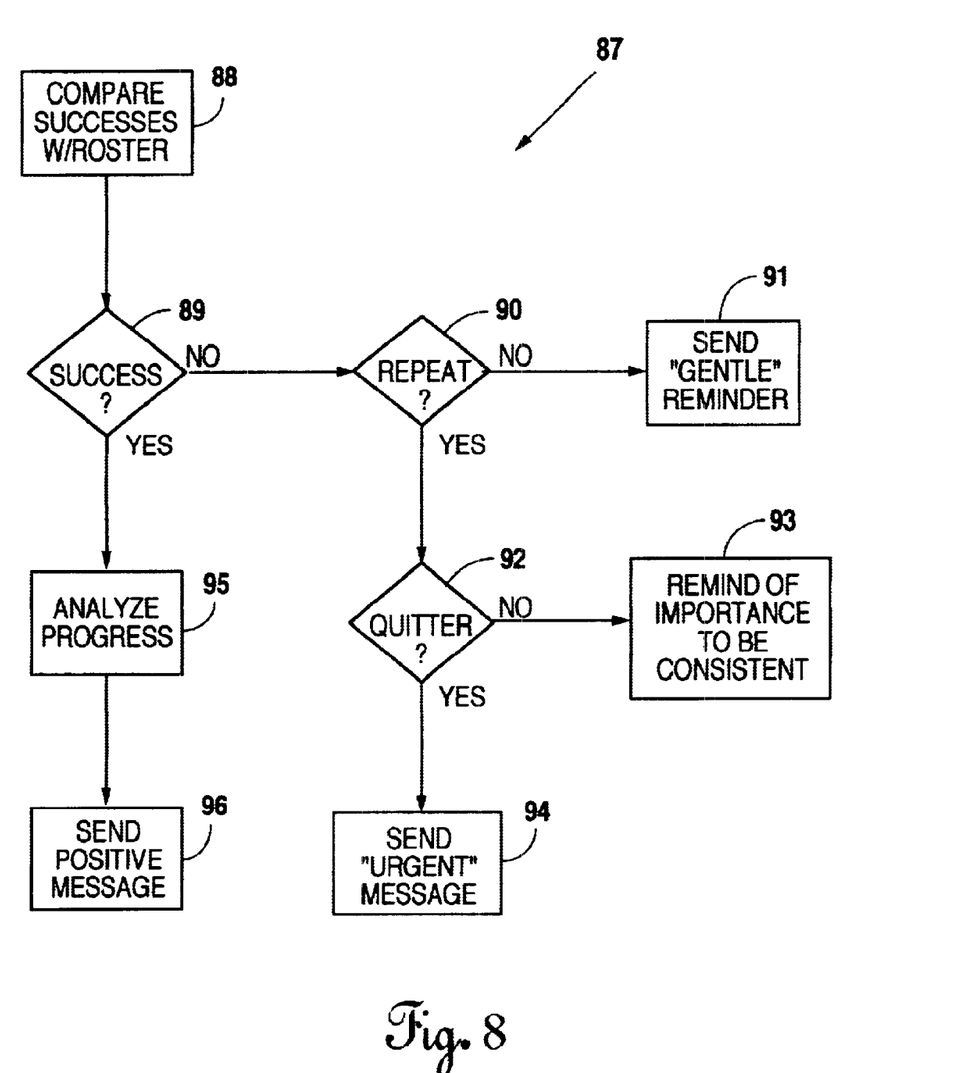
FIG. 8 shows, in a flowchart, a method for encouraging consistent compliance with the protocol of FIG. 4.

In an important aspect of the integrated weight loss system 20 of the present invention, software resident the host server 52 is programmed to monitor each user's compliance with the protocol 64. In this manner, the present invention is uniquely adapted to give maximum encouragement to each user for the successful attainment of each user's weight loss goals. As shown in FIG. 8, the reported successful completions are periodically compared with a membership roster (step 88). In this manner, delinquent members may be readily identified (step 89). Upon identification of a member as delinquent in following the protocol 64, it is desirable to determine whether the member is a repeat offender (step 90). In this manner, various types of messages may be automatically generated at the host server 52 for delivery by e-mail or otherwise through the Internet 54 to the delinquent user according to his or her risk for failure. To this end, if it is determined that the delinquent user is not a repeat offender, a "gentle" reminder and encouragement may be generated and transmitted through e-mail (step 91). If, on the other hand, the delinquent user is determined to be a repeat offender and therefore may be likely to quit the program, as may be indicated by multiple consecutive days missed, an "urgent" message may be generated (step 94). To the contrary, however, in the case of a repeat offender who has not missed multiple consecutive days of treatment, it may be desirable to send only a reminder stressing the importance of consistency in any weight management program (step 93). Finally, for those successfully completing a session, progress toward meeting goals may be analyzed (step 95) and appropriate "congratulatory" messages as well as encouragement, dietary suggestions and the like may be generated at the host server 52 and sent through the Internet 54 (step 96).

Figure 9:
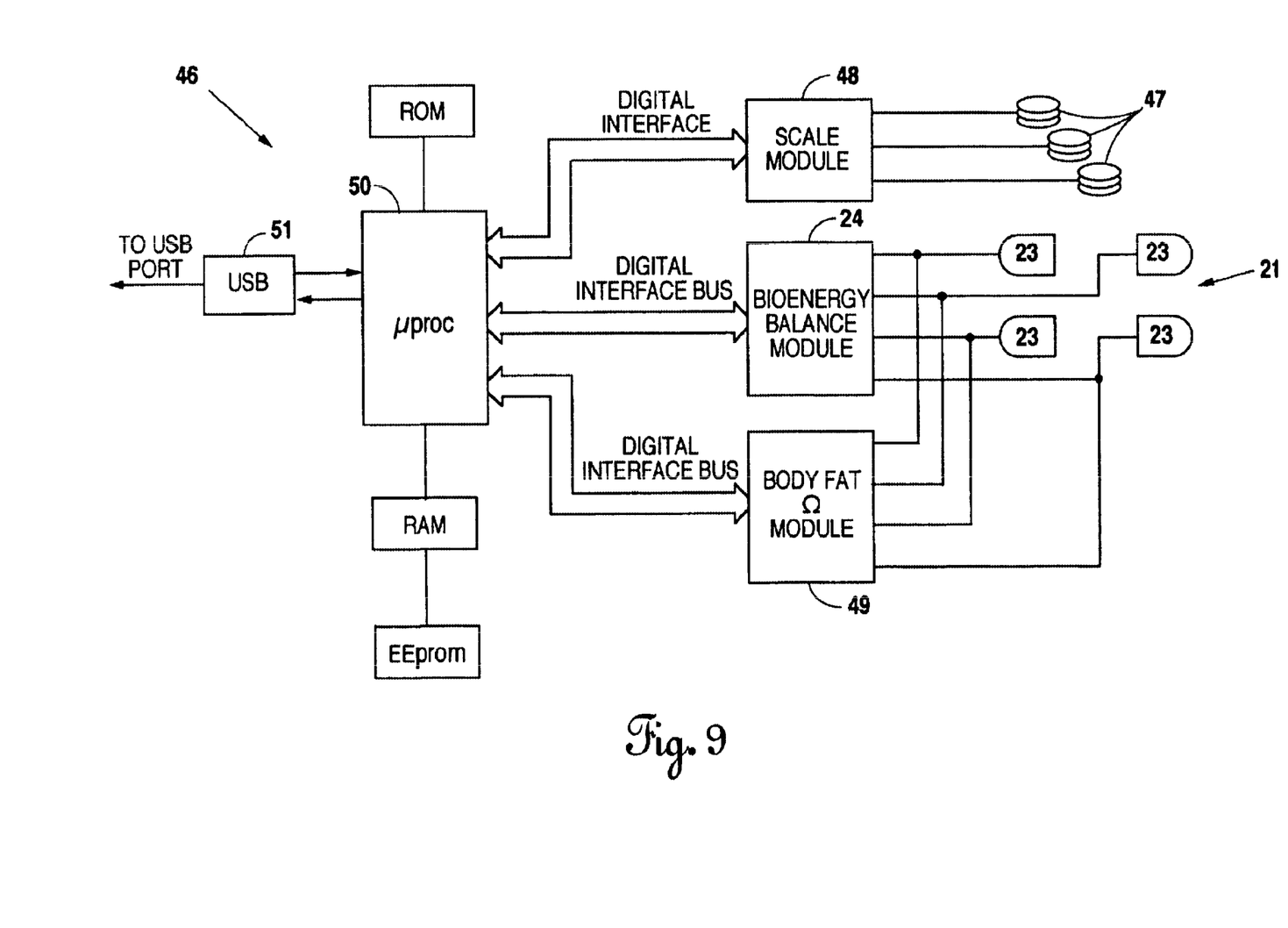
FIG. 9 shows, in a schematic block diagram, a fully integrated version of the electronic stimulation device of FIG. 3, including a scale and an interface to a user's personal computer.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. For example, those of an ordinary skill in the art will recognize that the digital scale 22, the stimulation control module 24 and a body fat analysis circuit 49 may all be implemented within a fully integrated stimulation device 46, as depicted in FIG. 9. Such a fully integrated stimulation device 46 preferably comprises load cells 47 and a scale circuit 48 and may be under the control of a microprocessor 50, which serves as a communication interface through appropriate hardware, such as a USB chipset 51, to corresponding hardware, such as, a USB port 57, at the user's personal computer 56. In this manner, all of the user-side equipment for the integrated weight loss system 20 may be conveniently packaged in an otherwise ordinary looking scale. In use, the user need only plug the fully integrated stimulation device 46 into the appropriate port on the user's personal computer 56 prior to beginning the protocol 64 as previously described. In any case, because the scope of the present invention is much broader than any particular embodiment, the foregoing detailed description should not be construed as a limitation of the scope of the present invention, which is limited only by the claims appended hereto.

What is claimed is:

1. A system for body fat management, said system comprising:
 a source of electrical current, said source having a plurally of electrical conductors for imparting the electrical current into a user's body;
 a controller for said source, said controller being adapted to selectively enable flow of the electrical current through said electrical conductors; and
 wherein:
  said controller is in communication with said source through a global communication network;
  said source is adapted for variation of the frequency of the electrical current; and
  said source of electrical current is embedded within a scale.

2. The system as recited in claim 1, wherein said scale is a digital scale.

3. The system as recited in claim 1, wherein said scale is adapted to report measurements made by said scale to said controller.

4. A system for body fat management, said system comprising:

a source of electrical current, said source having a plurality of electrical conductors for imparting the electrical current into a user's body;

a controller for said source, said controller being adapted to selectively enable flow of the electrical current through said electrical conductors; and wherein:

said controller is in communication with said source through the Internet;

said source is adapted for variation of the frequency of the electrical current; and said controller is adapted to generate and transmit through the Internet electronic messages for facilitating the user's utilization of said system.

5. The system as recited in claim 4, wherein said electronic messages comprise information related to the user's compliance with a protocol for utilization of said system.

6. The system as recited in claim 4, wherein said electronic messages comprise information related to the user's progress toward a dietary goal.

7. The system as recited in claim 4, wherein said controller is adapted to facilitate communication between different users.

8. A system for body fat management, said system comprising:

a source of electrical current, said source having a plurality of electrical conductors for imparting the electrical current into a user's body;

a controller for said source, said controller being adapted to selectively enable flow of the electrical current through said electrical conductors;

a detector adapted to monitor the flow of the electrical current through said electrical conductors; and wherein:

said source is adapted for variation of the frequency of the electrical current;

said source is adapted to report measurements from said detector to said controller; and said controller is adapted to control the variation of the frequency of the electrical current based upon the reported measurements from said detector.

9. The system as recited in claim 8, wherein said detector comprises a current detector.

10. The system as recited in claim 9, wherein said source is adapted for variation of the amplitude of the electrical current.

11. The system as recited in claim 10, wherein said controller is further adapted to control the variation of the amplitude of the electrical current.

\* \* \* \* \*